United States Patent [19]

Feniou et al.

[11] Patent Number: 4,638,082

[45] Date of Patent: Jan. 20, 1987

[54] METHOD OF PRODUCING THE P-CHLOROPHENOL ESTER OF P-CHLOROPHENOXYISOBUTYRIC ACID

[75] Inventors: Claude Feniou, Pessac; Patrick Descas, Bordeaux, both of France

[73] Assignee: Societe Corial, S.A., Paris, France

[21] Appl. No.: 832,688

[22] Filed: Feb. 25, 1986

[30] Foreign Application Priority Data

Feb. 28, 1985 [FR] France ............................ 85 03094

[51] Int. Cl.$^4$ ............................................. C07C 69/76
[52] U.S. Cl. ....................................................... 560/62
[58] Field of Search .......................................... 560/62

[56] References Cited

U.S. PATENT DOCUMENTS 3,448,110  6/1969  Griof ..................................... 560/62

FOREIGN PATENT DOCUMENTS

| 899903 | 5/1972 | Canada ................................. | 560/62 |
| 7332098 | 12/1968 | Japan .................................. | 560/62 |
| 7333742 | 10/1970 | Japan .................................. | 560/62 |
| 825875 | 12/1959 | United Kingdom .................. | 560/62 |

Primary Examiner—Paul J. Killos
Attorney, Agent, or Firm—Oblon, Fisher, Spivak, McClelland & Maier

[57] ABSTRACT

A novel method of producing the p-chlorophenol ester of p-chlorophenoxyisobutyric acid, which is a product useful in the treatment of hyperlipemias, is disclosed.

15 Claims, No Drawings

METHOD OF PRODUCING THE P-CHLOROPHENOL ESTER OF P-CHLOROPHENOXYISOBUTYRIC ACID

BACKGROUND OF THE INVENTION

1. Field of the Invention

The present invention relates to a novel method of producing dulofibrate, a product useful in the treatment of hyperlipermias.

2. Discussion of the Background

Dulofibrate is the p-chlorophenol ester of p-chlorophenoxyisobutyric acid. Its therapeutic use is described in French Pat. No. 77-06689, filed Mar. 8, 1977.

A number of methods of preparing esters of p-chlorophenoxyisobutyric acid (clofibric acid) are known. The alcohol esters of clofibric acid can be prepared from clofibric acid and the corresponding alcohol in the presence of $H^+$ ions, but this method is not applicable to phenol esters, and thus cannot be considered for manufacturing dulofibrate.

Another, more general method of preparing esters of clofibric acid consists of reacting a derivative of clofibric acid such as an acyl chloride or an acid anhydride, with a hydroxy-compound in the presence of, e.g., an organic tertiary amine, in a non-polar solvent such as toluene or benzene. This method can be employed for preparation of dulofibrate, and has been described in French Pat. No. 77-06689. A variant consists of reacting the clofibric acid and the hydroxy-compound which is to be esterified, in the presence of dicyclohexylcarbodiimide.

The clofibric acid is prepared generally from p-chlorophenol and acetone in the presence of sodium hydroxide and chloroform use (see Kleeman, A., and Engel, J., 1982, "Pharmaceutical substances—syntheses, patents, and applications" (in German, as "Pharmazeutische Wirkstoffe. Synthese. Patente. Anwendungen."), Vol. II., publ. Georg Thieme Verlag, New York).

Known methods for the preparation of clofibrate esters are lengthy and require numerous steps. Accordingly, in view of the usefulness of clofibrate esters, there is a strongly felt need for their ready preparation.

SUMMARY OF THE INVENTION

Accordingly, it is an object of this invention to provide a facile method for the preparation of dulofibrate.

It is another object of this invention to provide a method for the preparation of dulofibrate without isolation of intermediates.

It is another object of this invention to provide a method for the preparation of dulofibrate which is less costly than other existing methods.

The inventors have now surprisingly discovered a new method for the production of dulofibrate with satisfies all of the above objects of this invention, and other objects which will become apparent from the description provided below.

The present invention enables dulofibrate to be produced in two steps. Starting with p-chlorophenol, it provides the ready production of dulofibrate without need to isolate the intermediate product. It is much less costly and much more rapid than the classical methods of producing esters of clofibric acid. It is based on the following procedure: Preparing a salt of p-chlorophenol (preferably an alkaline salt) and reacting this phenolate, without isolating it, with an acyl halide of a haloisobutyric acid, preferably bromoisobutyric acyl bromide, in a non-polar solvent. The solvent may be benzene, dioxane, xylene or toluene. In this manner, the p-chlorophenol ester of clofibric acid is directly obtained.

DETAILED DESCRIPTION OF THE PREFERRED EMBODIMENTS

The following is a reaction scheme of the present process, where bromoisobutyric acyl bromide and sodium p-chlorophenolate are employed:

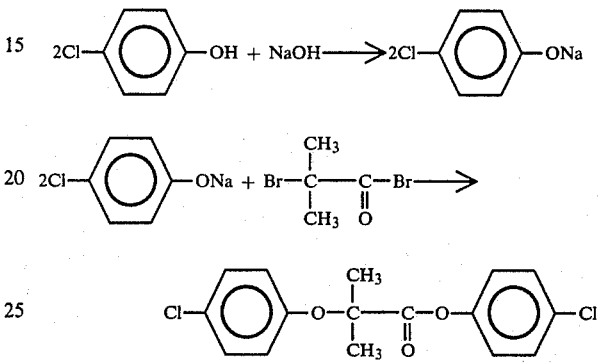

The method of the present invention employs an acyl halide of of a haloisobutyric acid. Any acyl halide of a haloisobutyric acid may be used. For example, acyl chlorides, acyl bromide and acyliodides can be used. Any haloisobutyric acid may also be used. For example chloroisobutyric acid, bromoisobutyric acid and iodoisobutyric acids may be used. The halide of the acyl halide part of the compound, and the halide of the haloisobutyric acid need not be the same.

Such a derivative was used in a method of preparing simfibrate, described in Japanese Patent JK No. 7783422 (Chem. Abstr. 87-201117), wherein propanediol is esterified by the acyl bromide of bromoisobutyric acid, and the dibromo derivative thus obtained is reacted with sodium p-chlorophenolate, to give simfibrate. The method of the present invention differs from the method described in the Japanese patent in that the brominated ester intermediate is not isolated, and the esterification and the O-alkylation of the p-chlorophenol are both carried out in the same step.

The salt of p-chlorophenol is prepared from an alkali metal base such as sodium hydroxide or potassium hydroxide, plus p-chlorophenol and water. The nonpolar solvent is introduced into the reaction medium during this first step, before any heating. At least 2 moles of p-chlorophenolate need be used per unit of haloisobutyric acid. So, for example, to prepare 2–3 moles of sodium p-chlorophenolate or potassium p-chlorophenolate, one employs 2–3 moles sodium hydroxide or potassium hydroxide, 75–150 ml water, 2–3 moles p-chlorophenol, and 1–2 liters of the non-polar solvent. The 1 mole of a haloisobutyric acyl halide is added to the suspension containing 2–3 moles sodium p-chlorophenolate or potassium p-chlorophenolate in a non-polar solvent. The reaction mixture is agitated until formation of the p-chlorophenolate of 2-bromo-2methylpropanoic acid, and then heated to temperatures of from 80° to 140° C., for a period of 1–3 hr. The temperature depends on the boiling temperature of the solvent. In a variant, before heating to 80°–140° C., one adds between 25 and 1000 ml, preferably between 50 and 500 ml of a dipolar aprotic solvent, such as dimethylformamide, acetone, nitromethane, dimethylacetamide, dimethylsulfoxide, tetramethylures or sulfolane per liter of the non-polar solvent.

Other featues of the invention will become apparent in the course of the following descriptions of exemplary embodiments which are given for illustration of the invention and are not intended to be limiting thereof.

EXAMPLE 1

20 ml water, 20.4 g 98% sodium hydroxide (0.5 mole) and 65 g p-chlorophenol (0.5 mole) were charged into a 1-liter flask. The reaction mixture was maintained at ambient temperature under agitation for 15 min. Then 400 ml toluene was added. The mixture was brought to reflux, and the water formed during the reaction was separated in a Dean and Starck trap.

When all the water had been separated, the mixture was cooled to ambient temperature. 30 ml (0.242 mole) of 2-bromo-2-methylpropanoyl bromide was added dropwise over 30 min. The reaction mixture was stirred further for 1 hr, and was then brought to reflux for 2 hr under vigorous stirring (because of the formation of a precipitate of sodium bromide). The reaction was monitored by thin layer silica chromotography, using a 50/50 mixture of petroleum ether and toluene ether a the eluent. The Rf values for dulofibrate and p-chlorophenol 2-bromo-2-methylpropanoate were 0.61 and 0.73, respectively.

The mixture was cooled to ambient temperature, 250 ml water was added, and the mixture was stirred. The aqueous phase was discarded. 250 mll N sodium hydroxide was added and the mixture was agitated. Again, the aqueous phase was discarded. This last operation was repeated once. Then 250 ml water was added, the mixture was agitated, and the aqueous phase was discarded. This last operation (water washing) was repeated until the discarded aqueous phase was neutral. The organic phase was the dried over calcium chloride. The resulting solution was filtered and was evaporated under reduced pressure.

250 ml 95% ethanol was added. Crystallization was allowed to occur, under agitation. The dulofibrate was filtered out and dried. 45.5 g dulofibrate was obtained, for a yield of 58% with respect to the 2-bromo-2-methylpropanoyl bromide.

EXAMPLE 2

The procedure was the same as in Example 1, up to the addition of the 30 ml (0.232 mole) of the 2-bromo-2methylpropanoyl bromide. Stirring of the reaction mixture was continued for 1 hr, and then 50 ml dimethylformamide was introduced. The mixture was heated to 115° C. for 1 hr, under vigorous agitation. The mixture was then cooled to ambient temperature. 250 ml water was added, and the mixture was stirred. The aqueous phase was discarded. 250 ml N sodium hydroxide was added and the mixture was agitated. Again, the aqueous phase was discarded. This last operation was repeated once. Then 250 ml water was added, the mixture was agitated, and the aqueous phase was discarded. This last operation (water washing) was repeated until the discarded aqueous phase was neutral. The organic phase was dried over calcium chloride.

The resulting solution was filtered and was evaporated under reduced pressure.

250 ml 95% ethanol was added. Crystallization was allowed to occur, under agitation. The dulofibrate was filtered out and dried.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A method for the preparation of the p-chlorophenol ester of p-chlorophenoxyisobutyric acid, comprising:
   (i) converting p-chlorophenol to a salt in the presence of a non-polar solvent, and
   (ii) reacting the said salt of p-chlorophenol with an acyl halide derivative of a haloisobutyric acid, wherein at least 2 moles of the said salt of p-chlorophenol are used per mole of the said haloisobutyric acid.

2. The method of claim 1, comprising converting the said p-chlorophenol to an alkali metal salt.

3. The method of claim 2, comprising converting the said p-chlorophenol to a sodium or a potassium salt.

4. The method of claim 1, comprising using as the non-polar solvent benzene, dioxane, xylene or toluene.

5. The method of claim 1, comprising using about 2 to 3 moles of the said salt of p-chlorophenol per mole of the haloisobutyric acid.

6. The method of claim 1, comprising using an acyl chloro, an acyl bromo or an acyl iodo derivative of a halobutyric acid.

7. The method of claim 1, comprising using chlorobutyric acid, bromobutyric acid or iodobutyric acid as the said halobutyric acid.

8. The method of claim 1, comprising using bromoisobutyric acid acyl bromide and sodium p-chlorophenolate.

9. The method of claim 1, comprising:
   (i) preparing sodium p-chlorophenolate from p-chlorophenol and sodium hydroxide, in water in the presence of a non-polar solvent, and
   (ii) reacting the said sodim p-chlorophenolate with bromoisobutyric acid acyl bromide.

10. The method of claim 9, comprising using benzene, dioxane, xylene or toluene as the said nonpolar solvent.

11. The method of claim 10, comprising using toluene.

12. The method of caim 1, comprising heating the reaction mixture containing the p-chlorophenolate, the haloisobutyric acid acyl halide and the non-polar solvent to a temperature of from 80° C. to 140° C. for 1 to 3 hours, after formation of the brominated intermediate ester.

13. The method of claim 12, comprising adding to the reaction medium 25 to 1000 ml of a dipolar aprotic solvent, per liter of the said non-polar solvent, prior to heating.

14. The method of claim 13, comprising using dimethylformamide, acetone, nitromethane, dimethylacetamide, dimethylsulfoxide, tetramethylurea or sulfolane as the said dipolar aprotic solvent.

15. The method of claim 14, comprising using dimethyl formamide.

* * * * *